United States Patent
Broderick et al.

(10) Patent No.: US 10,668,279 B2
(45) Date of Patent: Jun. 2, 2020

(54) MINIMINALLY INVASIVE DERMAL ELECTROPORATION DEVICE

(71) Applicant: Inovio Pharmaceuticals, Inc, Plymouth Meeting, PA (US)

(72) Inventors: Kate Broderick, San Diego, CA (US); Jay McCoy, Temecula, CA (US); Stephen V. Kemmerrer, San Diego, CA (US)

(73) Assignee: Inovio Pharmaceuticals, Inc., Plymouth Meeting, PA (US)

( * ) Notice: Subject to any disclaimer, the term of this patent is extended or adjusted under 35 U.S.C. 154(b) by 258 days.

(21) Appl. No.: 15/886,234

(22) Filed: Feb. 1, 2018

(65) Prior Publication Data
US 2018/0236225 A1    Aug. 23, 2018

Related U.S. Application Data

(62) Division of application No. 14/127,639, filed as application No. PCT/US2014/044539 on Jun. 28, 2012, now Pat. No. 9,913,978.
(Continued)

(51) Int. Cl.
*A61N 1/32* (2006.01)
*C12M 1/42* (2006.01)
(Continued)

(52) U.S. Cl.
CPC ........... *A61N 1/327* (2013.01); *A61N 1/0412* (2013.01); *A61N 1/0476* (2013.01); *C12M 35/02* (2013.01);
(Continued)

(58) Field of Classification Search
CPC ................ A61K 39/00; A61K 2039/51; A61K 2039/53; A61M 37/00; A61M 2037/0007;
(Continued)

(56) References Cited

U.S. PATENT DOCUMENTS

| 5,702,359 A | 12/1997 | Hofmann et al. |
| 5,908,629 A | 1/1999 | Michel et al. |

(Continued)

FOREIGN PATENT DOCUMENTS

| CN | 101563132 A | 10/2009 |
| EP | 1163024 A1 | 12/2001 |

(Continued)

OTHER PUBLICATIONS

Sanders et al., "Immunoglobulin Isotype-Specific Antibody Responses to Pneumococcal Polysaccharide Vaccine in Patients with Recurrent Bacterial Respiratory Tract Infections", Pediatric Research, vol. 37, No. 6, 1995, pp. 812-819.
(Continued)

*Primary Examiner* — Jason E Flick
(74) *Attorney, Agent, or Firm* — BakerHostetler

(57) ABSTRACT

The disclosure is directed to a device for electroporating and delivering one or more antigens and a method of electroporating and delivering one or more antigens to cells of epidermal tissues using the device. The device comprises a housing, a plurality of electrode arrays projecting from the housing, each electrode array including at least one electrode, a pulse generator electrically coupled to the electrodes, a programmable microcontroller electrically coupled to the pulse generator, and an electrical power source coupled to the pulse generator and the microcontroller. The electrode arrays define spatially separate sites.

20 Claims, 13 Drawing Sheets

Related U.S. Application Data

(60) Provisional application No. 61/502,198, filed on Jun. 28, 2011.

(51) Int. Cl.
*C12N 15/87* (2006.01)
*A61N 1/04* (2006.01)
*A61K 39/00* (2006.01)
*A61M 37/00* (2006.01)

(52) U.S. Cl.
CPC .......... *C12N 15/87* (2013.01); *A61K 2039/53* (2013.01); *A61M 2037/0007* (2013.01); *A61N 1/0424* (2013.01)

(58) Field of Classification Search
CPC ...... A61N 1/04; A61N 1/0404; A61N 1/0408; A61N 1/32; A61N 1/18; A61N 1/0412; A61N 1/0424; A61N 1/0476; A61N 1/327; C12M 35/02; C12N 15/87
USPC .......................................................... 604/20
See application file for complete search history.

(56) References Cited

U.S. PATENT DOCUMENTS

| | | |
|---|---|---|
| 6,207,157 B1 | 3/2001 | Gu et al. |
| 6,233,482 B1 | 5/2001 | Hofmann et al. |
| 6,241,701 B1 | 6/2001 | Hofmann |
| 6,256,533 B1 | 7/2001 | Yuzhakov et al. |
| 6,277,116 B1 | 8/2001 | Utely et al. |
| 6,309,633 B1 | 10/2001 | Ekwuribe et al. |
| 6,413,935 B1 | 7/2002 | Sette et al. |
| 6,493,402 B1 | 12/2002 | Fimoff |
| 6,520,950 B1 | 2/2003 | Hofmann et al. |
| 6,603,998 B1 | 8/2003 | King et al. |
| 7,657,317 B2 | 2/2010 | Thacker et al. |
| 7,713,266 B2 | 5/2010 | Elkins et al. |
| 8,133,216 B2 | 3/2012 | Knopp et al. |
| 9,596,920 B2 | 3/2017 | Shalev et al. |
| 2001/0023330 A1 | 9/2001 | Palti |
| 2002/0099323 A1 | 7/2002 | Dev et al. |
| 2002/0193833 A1 | 12/2002 | Dimmer et al. |
| 2004/0019371 A1 | 1/2004 | Jaafar et al. |
| 2005/0048651 A1 | 3/2005 | Ryttsen et al. |
| 2005/0123565 A1 | 6/2005 | Subramony et al. |
| 2006/0036210 A1 | 2/2006 | Zhang et al. |
| 2006/0084938 A1 | 4/2006 | Zhang et al. |
| 2006/0264807 A1 | 11/2006 | Westersten et al. |
| 2007/0185432 A1 | 8/2007 | Etheredge, III et al. |
| 2008/0091135 A1 | 4/2008 | Draghia-Akli et al. |
| 2008/0132885 A1 | 6/2008 | Rubinsky et al. |
| 2008/0312580 A1 | 12/2008 | Barsness et al. |
| 2010/0010480 A1 | 1/2010 | Mehta et al. |
| 2010/0298761 A1 | 11/2010 | Staal et al. |
| 2011/0009807 A1 | 1/2011 | Kjeken et al. |
| 2011/0023330 A1 | 2/2011 | McBride |
| 2011/0046539 A1 | 2/2011 | Atanasoska et al. |
| 2011/0150924 A1* | 6/2011 | Della Rocca .......... A61K 39/39 424/204.1 |
| 2012/0059255 A1 | 3/2012 | Paul et al. |
| 2012/0323165 A1 | 12/2012 | Broderick et al. |
| 2013/0066296 A1* | 3/2013 | Broderick ............ A61K 39/145 604/501 |

FOREIGN PATENT DOCUMENTS

| | | |
|---|---|---|
| JP | 2000-503586 A | 3/2000 |
| JP | 2002-535100 A | 10/2002 |
| JP | 2007-509704 A | 4/2007 |
| JP | 2009508595 A | 3/2009 |
| JP | 2010-505518 A | 2/2010 |
| JP | 2010-506660 A | 3/2010 |
| WO | 93/21948 A1 | 11/1993 |
| WO | 2005010161 A2 | 2/2005 |
| WO | 2011109406 A1 | 9/2011 |

OTHER PUBLICATIONS

Pirofski et al., "Analysis of Human Monoclonal Antibodies Elicited by Vaccination with a Cryptococcus neoformans Glucuronoxylomannan Capsular Polysaccharide Vaccine", vol. 63, No. 8, Aug. 1995, pp. 3005-3014.

"The Jordan Report: Accelerated Development of Vaccines 1995", National Institutes of Health, Division of Microbiology and Infectious Diseases, National Institute of Allergy and Infectious Diseases, 1995, 85 Pages.

Devi et al., "Capsular Polysaccharide-Protein Conjugate Vaccines of Carbotype 1 Vibrio vulnificus: Construction, Immunogenicity, and Protective Efficacy in a Murine Model", Aug. 1995, vol. 63, No. 8, pp. 2906-2911.

Bartoloni et al., "Immunogenicity of Meningococcal B Polysaccharide Conjugated to Tetanus Toxoid or CRM197 via Adipic Acid Dihydrazide", Vaccine, vol. 13, No. 5, pp. 463-470.

* cited by examiner

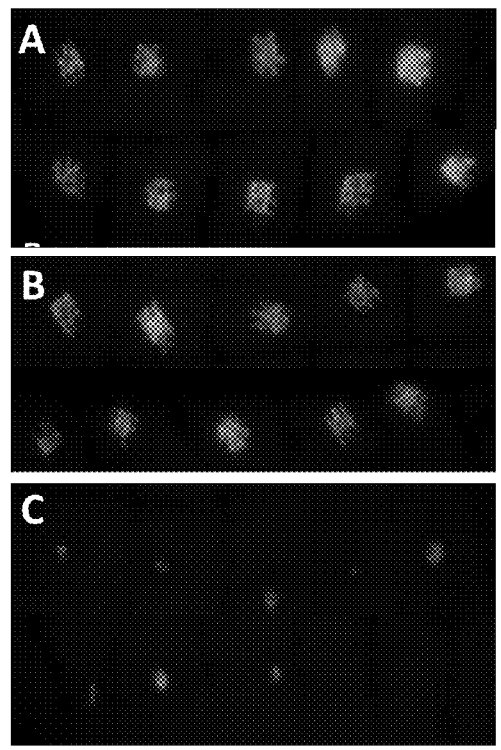
Fig. 5A
Fig. 5B
Fig. 5C
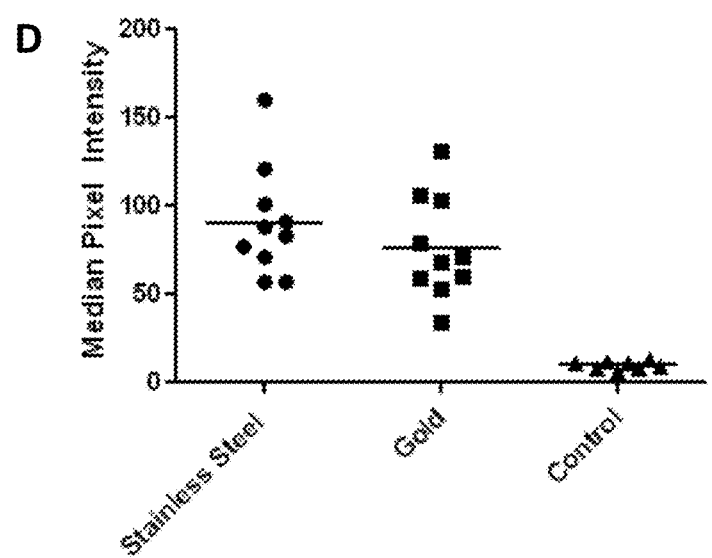
Fig. 5D

Fig. 7A
Fig. 7B
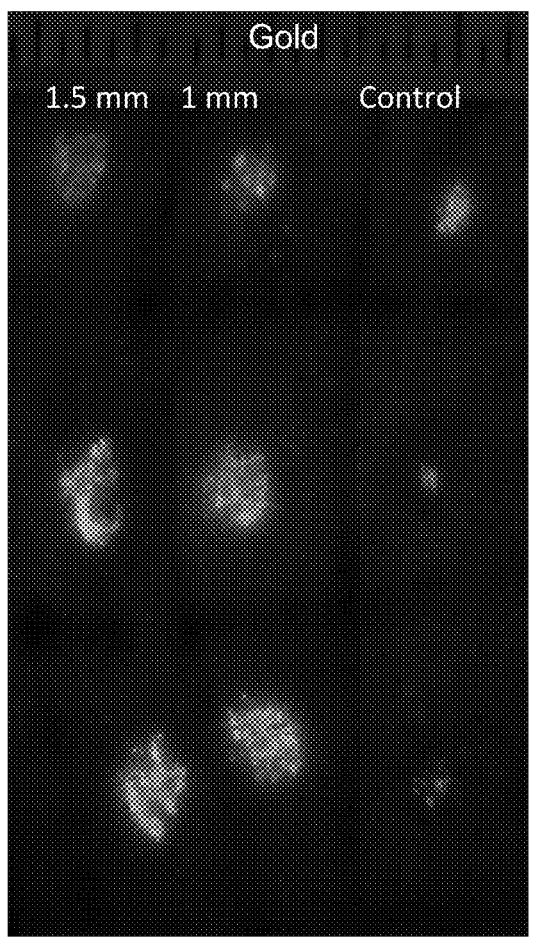
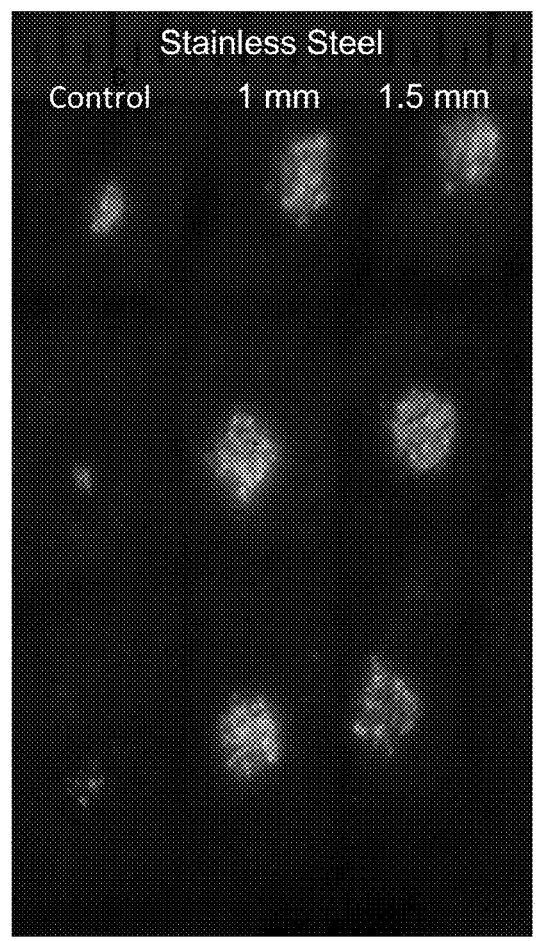
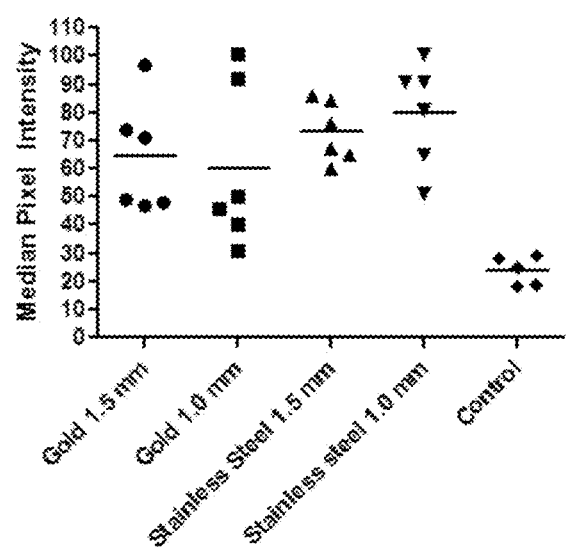
Fig. 7C

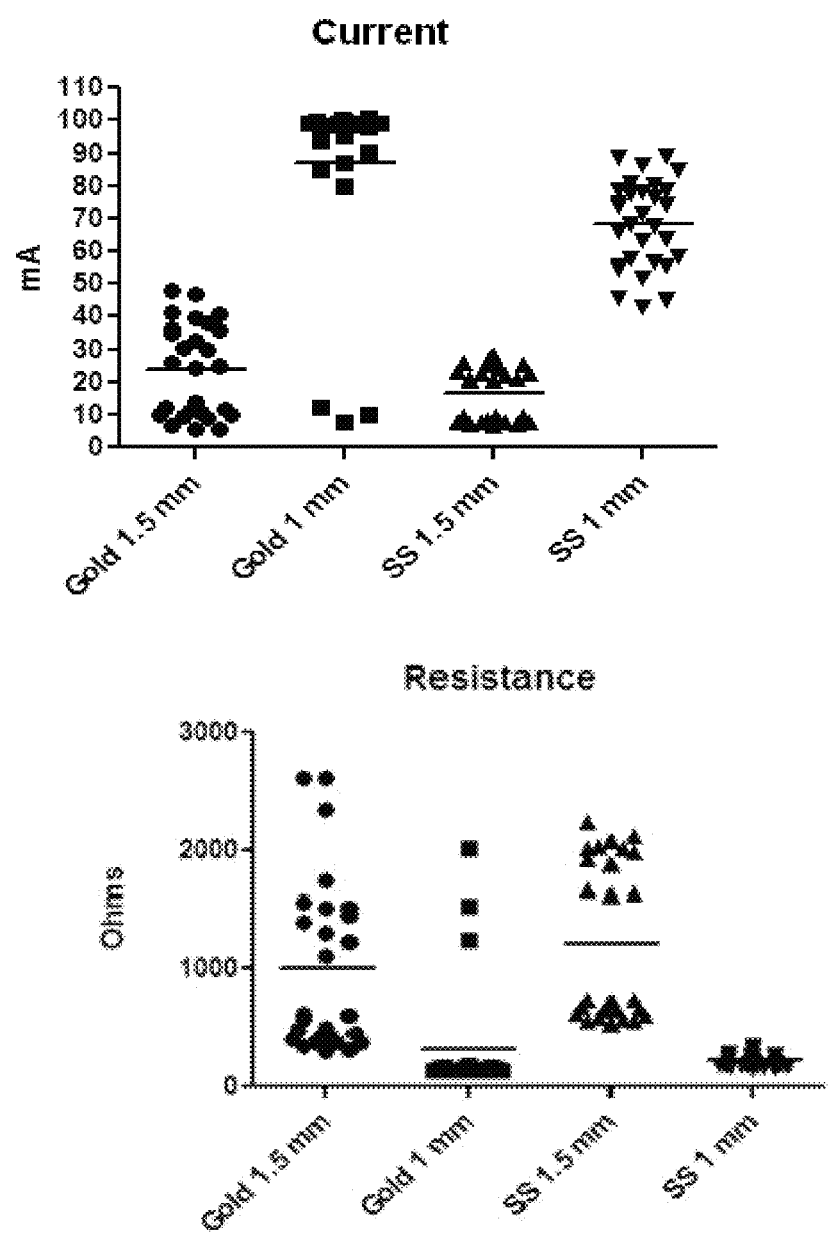

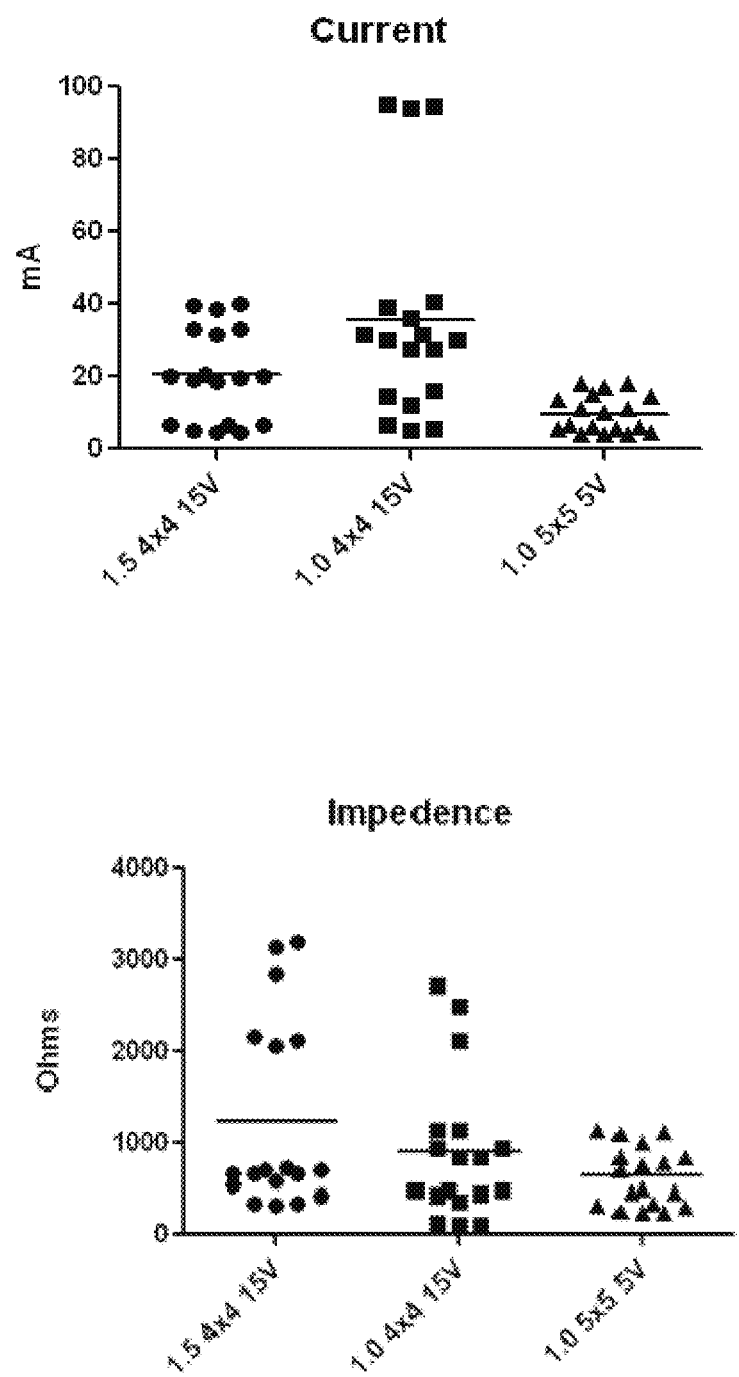

Fig. 10A
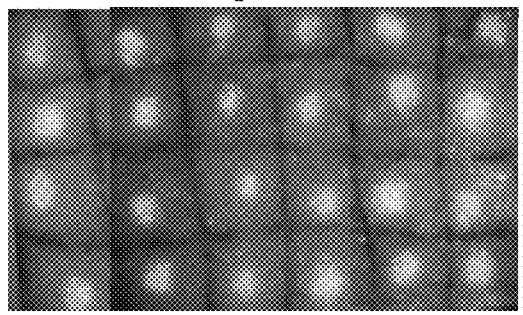
| 4x4 | 4x4 | 4x4 | 4x4 | 5x5 | 5x5 |
| 1.5mm | 1.5mm | 1.0mm | 1.0mm | 1.0mm | 1.0mm |
| 15v | 5v | 15v | 5v | 15v | 5v |
Fig. 10B
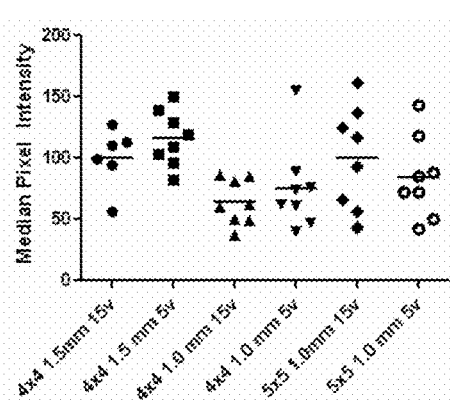
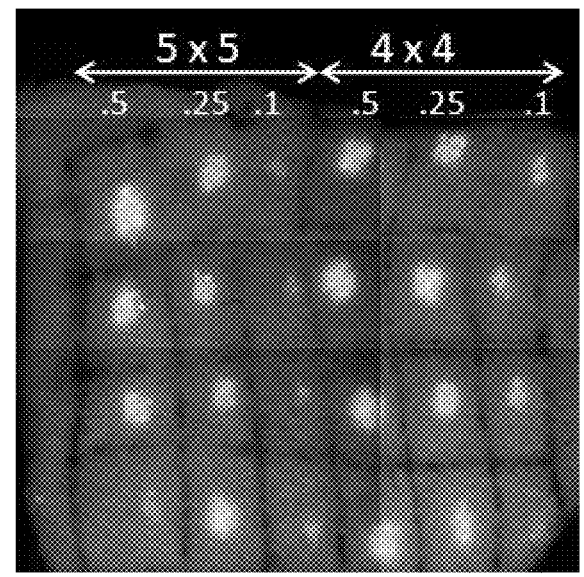
Fig. 11A
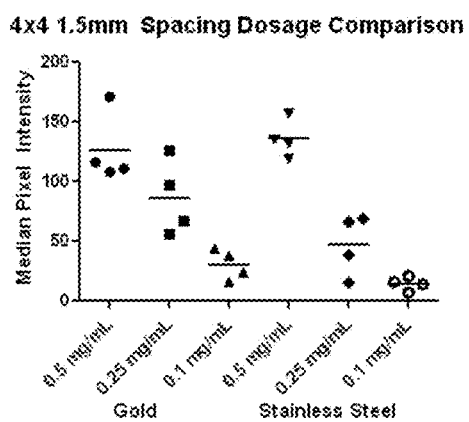
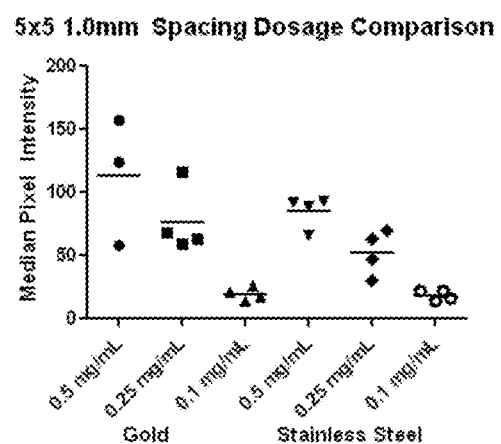
Fig. 11B

MINIMINALLY INVASIVE DERMAL ELECTROPORATION DEVICE

CROSS-REFERENCE TO RELATED APPLICATIONS

This application is a divisional of U.S. patent application Ser. No. 14/127,639, filed Apr. 14, 2014, which claims the benefit of PCT Application No. US2012/044539, filed Jun. 28, 2012, which claims the benefit of U.S. Provisional Application No. 61/502,198, filed Jun. 28, 2011, the entire content of each of which is incorporated herein by reference.

FEDERALLY-SPONSORED RESEARCH AND DEVELOPMENT

Activities relating to the development of the subject matter of this invention were funded at least in part by U.S. Government, Army Contract No. W81XWH-11-C-0051, and thus the U.S. may have certain rights in the invention.

FIELD OF THE INVENTION

The present invention relates to an electroporation device that is capable of delivering one or more plasmid vaccines simultaneously at spatially separate sites in a tolerable manner.

BACKGROUND

A major obstacle to effective vaccination via antigenic plasmids is the need of the DNA vaccine to be delivered intracellularly. The delivery of naked DNA through a standard intramuscular injection is notoriously inefficient outside of rodent models. Historically, this has led to an inability to achieve robust immune responses in large mammals and humans. Several strategies have been developed to enhance the expression of DNA-based vaccines, such as codon-optimization, RNA optimization, leader sequence addition and the development of optimized consensus sequences. These optimization strategies can lead to improved, cross-reactive immune responses. The addition of co-delivered gene-based molecular adjuvants is another area where an augmentation of resulting immune responses frequently occurs. Despite the improvements in vector design and use of molecular adjuvants, there is still a clear need for an efficient method of administration of DNA vaccines that results in high level expression of the plasmid in the desired cell type of the desired tissue, most commonly, muscle, tumor or skin.

Drug delivery to dermal tissue (intradermal) is an attractive method in a clinical setting for a number of reasons. The skin is the largest organ of the human body, the most accessible, and easily monitored, as well as being highly immuno-competent. However, the impervious, barrier function of the skin has been a major obstacle to efficient trans-dermal drug delivery.

Human skin comprises approximately 2 $m^2$ in area and is around 2.5 mm thick on average, making it the largest organ of the human body. Conventionally, the skin has two broad tissue types, the epidermis and the dermis. The epidermis is a continually keratinizing stratified epithelium. The outermost layer of skin is the stratum corneum (SC) and functions as the primary barrier. The SC is a 15-30 cell thick layer of non-viable but biochemically active corneocytes. The other three strata of the epidermis (*S. granulosum, S. spinosum, S. basale*) all contain ketatinocytes at different stages of differentiation as well as the immune Langerhans cells and dermal dendritic cells.

Both physical and chemical methods for trans-dermal drug delivery and gene delivery have been detailed by groups worldwide. Iontophoresis, lipid delivery and gene gun are such examples. A physical method to temporarily increase skin permeability is electroporation ("EP"). Electroporation involves the application of brief electrical pulses that result in the creation of aqueous pathways within the lipid bi-layer membranes of mammalian cells. This allows the passage of large molecules, including DNA, through the cell membrane which would otherwise be less permeable. As such, electroporation increases the uptake or the extent to which drugs and DNA are delivered to their target tissue.

Although the precise mechanism by which electroporation enables cell transformation has not been elucidated, a proposed theoretical model involves a poration event due to the destabilization of the membrane, followed by the electrophoretic movement of charged molecules into the cell. For electroporation to occur, the formation of pores requires that a threshold energy be achieved and the movement produced by the electrophoretic effect depends upon both the electric field and the pulse length.

In the case of DNA vaccines, electroporation has been shown to quantitatively enhance immune responses, increase the breadth of those immune responses as well as improve the efficiency of dose. More recently, the DNA-EP platform has been successfully translated into the human clinical setting and has demonstrated significantly improved immune responses in several vaccine studies. Therefore, there has developed a need for a dermal electroporation device that would be considered tolerable, user-friendly and easily amenable to mass production, while continuing to achieve high transfection rates resulting in robust immune responses.

Although a number of intramuscular devices have now successfully entered clinical trials, the procedure is generally considered invasive and painful. To be considered amenable to mass vaccination, especially in a pediatric setting, a solution for a more tolerable electroporation method is needed. Accordingly, an effective dermal electroporation device that is capable of delivering a multi-agent DNA vaccine in a tolerable manner is desirable.

SUMMARY OF THE INVENTION

The present disclosure is directed to a device for electroporating and delivering one or more antigens. The device comprises a housing, a plurality of electrode arrays projecting from the housing, each electrode array including at least one electrode, a pulse generator electrically coupled to the electrodes, a programmable microcontroller electrically coupled to the pulse generator, and an electrical power source coupled to the pulse generator and the microcontroller. The electrode arrays define spatially separate sites. The electrodes are configured to deliver an electroporating pulse to cells of epidermal tissues. The microcontroller is configured to adjust parameters of the electroporating pulse of each electrode array independently.

The present disclosure is also directed to a method of electroporating and delivering one or more antigens to cells of epidermal tissues using the device described herein. In embodiments, the antigens generally include DNA vaccine plasmids, peptides, small molecules, and combinations thereof. The method comprises administering the one or more antigens to the cells of the epidermal tissues, contacting the epidermal tissues with the electrodes, and delivering the electroporating pulses.

BRIEF DESCRIPTION OF THE DRAWINGS

FIGS. 5A, 5B, and 5C are fluorescent micrographs of green fluorescent protein (GFP) expression following injection and electroporation of plasmids using an MID with (FIG. 5A) stainless steel electrodes or (FIG. 5B) gold electrodes or with (FIG. 5C) injection only and no electroporation as a control. FIG. 5D is a chart showing GFP pixel intensity calculated from the flourescent micrographs illustrated in FIGS. 5A, 5B, and 5C.

FIGS. 7A, 7B, and 7C are fluorescent micrographs of GFP expression following injection and electroporation of plasmids using an MID with 1.5 mm or 1 mm electrode spacing and (FIG. 7A) stainless steel electrodes or (FIG. 7B) gold electrodes. A set with injection only and no electroporation was used as a control. GFP pixel intensity was calculated (FIG. 7C).

FIG. 8 shows graphs of current and resistance for MIDs with 1.5 mm or 1 mm electrode spacing. Electrodes were either gold or stainless steel (SS) in composition.

FIG. 9 shows graphs of current and impedence for MIDs with 1.5 mm or 1 mm electrode spacing at 5 or 15 volts.

FIG. 10A shows fluorescent micrographs of GFP expression following injection and electroporation of plasmids using an MID with 1.5 mm or 1 mm electrode spacing at 5 or 15 volts. FIG. 10B is a chart showing GFP pixel intensity calculated form the fluorescent micrographs illustrated in FIG. 10A.

FIG. 11A shows fluorescent micrographs of GFP expression following injection and electroporation of different concentrations (0.5, 0.25, and 0.1 mg/mL) of plasmid using an MID with 1.5 mm or 1 mm electrode spacing at 15 volts. FIG. 11B shows GFP pixel intensity calculated from the fluorescent micrographs illustrated in FIG. 11A.

FIG. 12A is a skin biopsy in an untreated animal at 20× magnification. FIG. 12B is a skin biopsy from an animal treated with plasmid expression GFP at 20× magnification. FIG. 12C is the sample in FIG. 12B but at 40× magnification.

DETAILED DESCRIPTION

Figure 1A:
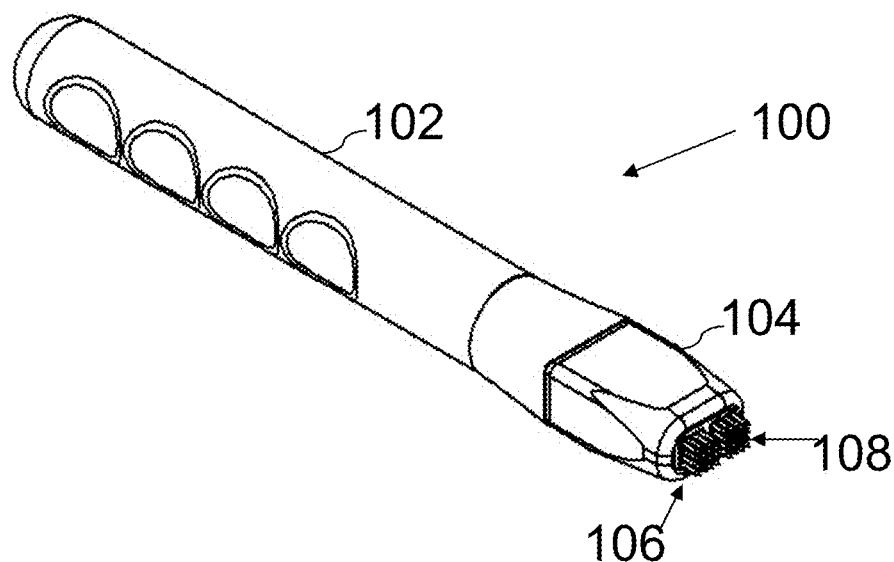
FIGS. 1A, 1B, and 1C are perspective views of a minimally invasive device (MID) for EP according to an embodiment.

The present invention is directed to an electroporation device that can provide heterogeneous intradermal delivery of antigens to a mammal. One or more antigens can be delivered simultaneously at spatially separated sites in a tolerable manner via a minimally invasive device (MID) having a plurality of electrode arrays. The electrode arrays are configured to vary the electroporating pulse from array to array. For example, each electrode array can be independently and selectively activated or controlled. Thus, the MID enables a heterogeneous delivery of antigens. Dermal electroporation via this MID reflects a clinically acceptable method to effectively deliver vaccines to the skin of a subject. This device is amenable to delivering multiple vaccines in multiple forms (nucleic acid, protein, small molecules, or a combination thereof) simultaneously while removing potential concerns with immune-interference resulting from the co-delivery of multiple antigens. It also allows the ability to deliver higher doses of a single antigen during a single treatment.

1. Definitions

The terminology used herein is for the purpose of describing particular embodiments only and is not intended to be limiting. As used in the specification and the appended claims, the singular forms "a," "and" and "the" include plural references unless the context clearly dictates otherwise.

For the recitation of numeric ranges herein, each intervening number therebetween with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The term "electroporation" as used herein refers to the use of a transmembrane electric field pulse to induce microscopic pathways (pores) in a bio-membrane; the pores' presence allows biomolecules such as plasmids, oligonucleotides, siRNA, drugs, ions, and water to temporarily pass from one side of the cellular membrane to the other.

The term "minimally invasive" as used herein refers to a limited penetration by the needle electrodes of the provided EP device, and can include noninvasive electrodes (or nonpenetrating needles). Preferably, the penetration is to a degree that penetrates through stratum corneum, and preferably enters into the outermost living tissue layer, the stratum granulosum, but does not penetrate the basal layer. The penetration depth preferably does not exceed 0.1 mm, and in some embodiments the penetration depth ranges from about 0.01 mm to about 0.04 mm to break through stratum corneum. This can be accomplished using an electrode that has a trocar end ground to provide a sharp point that allows penetration through the stratum corneum but avoids a deeper penetration.

The terms "tolerable" and "nearly painless" are used interchangeably herein, and when referring to EP, mean a substantially lower level of pain associated with EP than with typically available EP devices. More specifically, a tolerable or near painless EP is the result of combination of using the device described herein, avoiding EP of muscle, along with delivering low electrical fields to the epidermal layers between the stratum corneum and the basal layers.

Preferably the electrical fields will comprise low voltage levels, for example from 0.01 V to 70 V, or from 1 V to 15 V. When measured using a visual analog scale, subjects experiencing EP with the device described herein according to the methods provided herein experience pain levels that are within 20% (of the full scale) from their painless or pain free score, or for example, within 2 points, with 0-10 full scale, and preferably within 10% from their painless score.

The term "substantially prevents damage" is used herein to refer to an amount of energy that is delivered by the described devices to the target cells to electroporate said cells and cause minimal discernible damage to same cells. Preferably, there is no discernable macroscopic histological damage or alteration to such cells.

2. Minimally Invasive Device

Figure 1B:
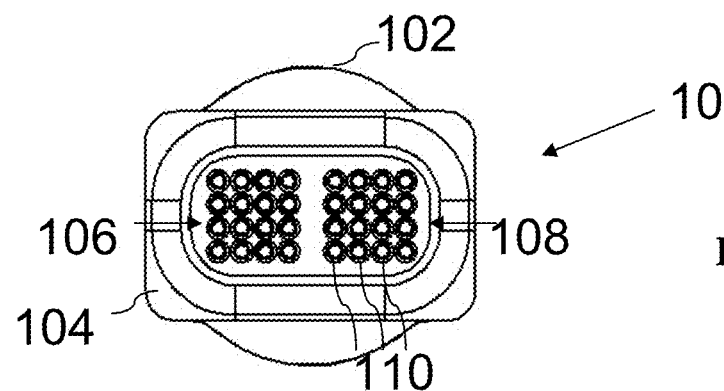
Figure 1C:
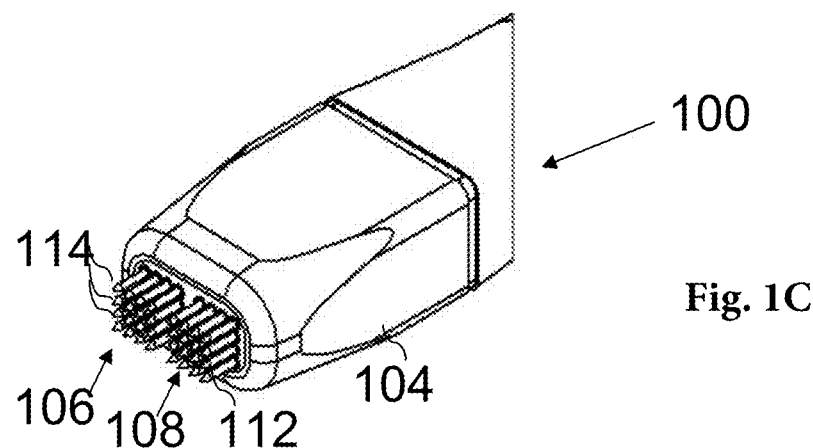

The present invention is directed to a minimally invasive device (MID) having a plurality of electrode arrays that are configured to vary the electroporating pulse from array to array. FIGS. 1A, 1B, and 1C disclose an MID 100 having a plurality of electrode arrays for electroporating and delivering one or more antigens. The MID 100 comprises a housing 102 having a tip portion 104, a plurality of electrode arrays 106, 108, coupled to the tip portion 104, each electrode array 106, 108 including electrodes 110 arranged in a square 4×4 pattern. In some embodiments, one or both of the tip portion 104 and the electrodes 110 can be detached from the rest of the MID 100, e.g., for sterilizing after use so that the detached parts can be used again. Alternatively, one or both of the tip portion 104 and the electrodes 110 can be for a single use.

The electrode arrays 106, 108 define spatially separate sites. Although FIGS. 1A, 1B, and 1C illustrate the MID 100 as including two electrode arrays 106, 108, in other embodiments the MID 100 can include more than two electrode arrays, e.g., three or more, four or more, five or more, six or more, seven or more, eight or more, nine or more, or ten or more electrode arrays.

In some embodiments, each array 106, 108 can include a 4×4 array of electrodes 110 having a respective length of 0.1 mm, 0.2 mm, 0.3 mm, 0.4 mm, 0.5 mm, 1.0 mm, 1.5 mm, 2.0 mm, 2.5 mm, 3.0 mm, 3.5 mm, 4.0 mm, 4.5 mm, 5 mm, 6.0 mm, 7.0 mm, 8.0 mm, 9.0 mm, or 10.0 mm. Although in the illustrated embodiment each array 106, 108 includes a 4×4 array of electrodes 110, i.e., 16 electrodes 110, in other embodiments, each of the arrays 106, 108 can respectively include other numbers and/or patterns of electrodes 110. For example, each of the arrays 106, 108 can respectively include electrodes 110 arranged in a pattern of 1×1, 1×2, 1×3, 1×4, 1×5, 1×6, 1×7, 1×8, 1×9, 1×10, 2×1, 2×2, 2×3, 2×4, 2×5, 2×6, 2×7, 2×8, 2×9, 2×10, 3×1, 3×2, 3×3, 3×4, 3×5, 3×6, 3×7, 3×8, 3×9, 3×10, 4×1, 4×2, 4×3, 4×4, 4×5, 4×6, 4×7, 4×8, 4×9, 4×10, 5×1, 5×2, 5×3, 5×4, 5×5, 5×6, 5×7, 5×8, 5×9, 5×10, 6×1, 6×2, 6×3, 6×4, 6×5, 6×6, 6×7, 6×8, 6×9, 6×10, 7×1, 7×2, 7×3, 7×4, 7×5, 7×6, 7×7, 7×8, 7×9, 7×10, 8×1, 8×2, 8×3, 8×4, 8×5, 8×6, 8×7, 8×8, 8×9, 8×10, 9×1, 9×2, 9×3, 9×4, 9×5, 9×6, 9×7, 9×8, 9×9, 9×10, 10×1, 10×2, 10×3, 10×4, 10×5, 10×6, 10×7, 10×8, 10×9, 10×10, or multiples of 11-100 and any combination thereof. The patterns can be arranged in various shapes such as squares, triangles, rectangles, parallelograms, circles or any other geometric shape. The needle-shaped electrodes 110 can comprise gold, platinum, titanium, stainless steel, aluminum, or any other conductive metal. The electrodes can be coated or plated with a metal such as gold, copper, platinum, silver, or any other conductive metal.

In some embodiments, each electrode 110 is needle-shaped. That is, the electrodes 110 each include a shaft 112 and a tapered tissue-penetrating or trocar end 114. Although FIG. 1B illustrates the electrodes 110 as being generally cylindrical, in other embodiments, at least one of the electrodes 110 can assume any geometric form, including, but not limited to, a semi-cylindrical, a regular polyhedral, and an irregular polyhedral shape, derivatives thereof, and combinations thereof. The tissue-penetrating end 114 can facilitate the electrodes 110 penetrating through the stratum corneum and reaching the stratum granulosum. In some embodiments, the tissue-penetrating end 114 allows the electrode 110 to penetrate through the stratum corneum but avoids deep penetration. To this end, the tissue-penetrating end 114 can have a length of about 0.1 mm or less, or about 0.01 mm to about 0.04 mm.

The illustrated electrodes 110 are configured to deliver an electroporating pulse to cells of epidermal tissues. In some embodiments, the electroporating pulses are associated with an electrical field that substantially prevents damage in the cells of the epidermal tissues. In further embodiments, the electroporating pulses are associated with an electrical potential that is nearly painless as measured by a visual analog scale. The visual analog scale is essentially a 100-mm-long horizontal line on which 0 mm indicates no pain and 100 mm indicates the worst pain. Near painless is a score using the visual analog scale that produces a mean score of about 20 mm or less (within a 95% confidence interval), and preferably 10 mm or less (within a 95% confidence interval).

In some embodiments, adjoining electrodes 110 are spaced apart from one another at a distance of no more than about 1.5 mm. In further embodiments, adjoining electrodes 110 are spaced apart from one another at a distance of no more than about 1.0 mm. A shorter distance between the electrodes 110 means that the electrodes 110 are packed in a more compact manner, which can increase the efficacy of the MID 100 and therefore can be desirable. In some embodiments, each electrode 110 can be spaced apart from each adjacent electrode 110 at a distance of 150 mm or less, from 100 mm to 1.0 mm, from 50 mm to 1.0 mm, from 40 mm to 1.0 mm, from 30 mm to 1.0 mm, from 20 mm to 1.0 mm, from 10 mm to 1.0 mm, from 5.0 mm to 2.0 mm, from 5.0 mm to 1.0 mm, approximately 2.0 mm, approximately 1.5 mm, or approximately 1.0 mm.

Figure 2:
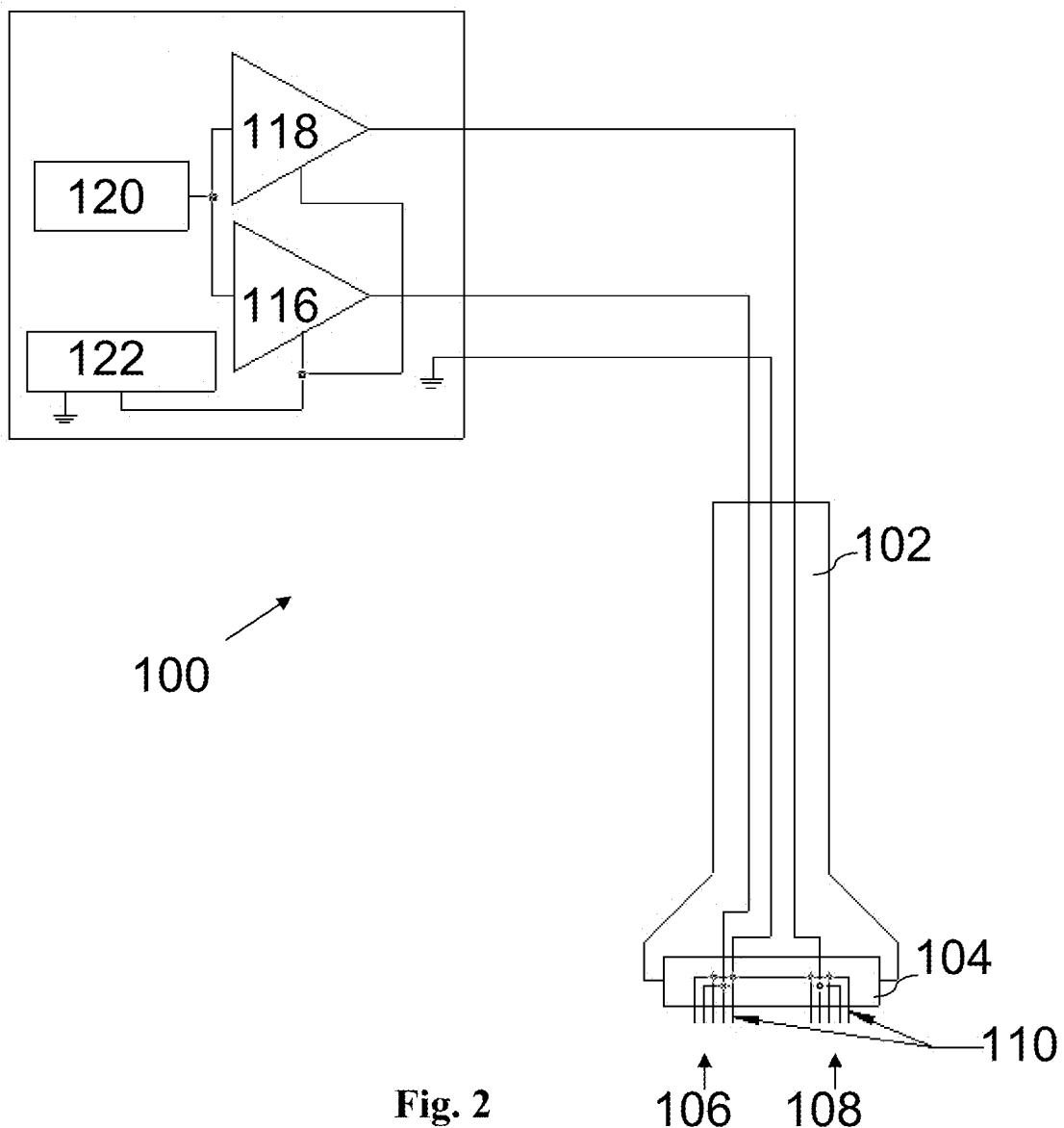
FIG. 2 is a schematic illustration of an electrical system of the embodiment of FIGS. 1A, 1B, and 1C.

Referring also to FIG. 2, pulse generators 116, 118 are electrically coupled to respective electrode arrays 106, 108. In some embodiments, at least one of the pulse generators 116, 118 can be the Elgen 1000 (Inovio Pharmaceuticals, Inc., Blue Bell, Pa.) pulse generator (not shown). In other embodiments, however, the electroporating pulse can be generated using other suitable mechanisms. In the illustrated embodiment, a programmable microcontroller 120 is electrically coupled to the pulse generators 116, 118. In response to an input condition/signal, the microcontroller 120 is capable of adjusting EP parameters of each electrode array 106, 108 independently, depending on the usage requirements or preferences for each electrode array 106, 108. Thus, the microcontroller 120 is configured to vary the electroporating pulse from array to array. For example, the pulse voltage, current, duration, and quantity of the applied electrical pulses can be varied from array to array so as to vary the Joules per $cm^3$ applied at each injection site. In some embodiments, the microcontroller 120 is configured to deliver the electroporating pulses substantially simultaneously. In the illustrated embodiment, each electrode array 106, 108 is driven with a respective pulse generator 116, 118. The MID 100 also includes an electrical power source 122 coupled to the pulse generators 116, 118 and the microcontroller 120 for providing electrical power. In the illustrated embodiment, the electrical power source 122 is a high and low voltage supply, although other power sources performing the same function as the electrical power source 122 disclosed herein can be used instead.

In some embodiments, the electroporating pulse of each electrode array 106, 108 is associated with an electrical potential of 0.01 V to 70 V, 0.01 V to 50 V, 0.01 V to 40 V, 0.01 V to 30 V, 0.01 V to 20 V, 0.01 V to 15 V, 0.1 V to 70 V, 0.1 V to 50 V, 0.1 V to 40 V, 0.1 V to 30 V, 0.1 V to 20 V, 0.1 V to 15 V, 1V to 30V, 1V to 20V, 1 V to 15 V, 15V to 30V, or 15V to 30V. In further embodiments, the electrical potential is preferably low so that the EP is tolerable or nearly painless as measured by a visual analog scale, yet sufficiently high so as to effect transfection of the cells in the epidermal tissues. For example, the electrical potential can be 5V, 10V, 15 V, or in some embodiments 20V, when adjacent electrodes 110 of the MID 100 are spaced apart by 1.0 mm to 2.0 mm.

In some embodiments, each electroporating pulse of each electrode array 106, 108 is associated with an electrical current of 0.1 mA to 100 mA, 0.2 mA to 100 mA, 0.5 mA to 100 mA, 1 mA to 100 mA, 1 mA to 80 mA, 1 mA to 60 mA, 1 mA to 50 mA, 1 mA to 40 mA, 1 mA to 30 mA, 10 mA to 50 mA, 10 mA to 40 mA, 10 mA to 30 mA, 10 mA to 20 mA, or 10 mA to 15 mA, or approximately 10 mA, or in some embodiments approximately 20 mA. Like the electrical potential, the electrical current is preferably low so that the EP is tolerable or nearly painless as measured by a visual analog scale, yet sufficiently high so as to effect transfection of the cells in the epidermal tissues.

In some embodiments, the electroporating pulse of each electrode array 106, 108 is associated with a duration of from 5 ms to 250 ms, 10 ms to 250 ms, 20 ms to 250 ms, 40 ms to 250 ms, 60 ms, to 250 ms, 80 ms to 250 ms, 100 ms to 250 ms, 20 ms to 150 ms, 40 ms to 150 ms, 60 ms to 150 ms, 80 ms to 150 ms, 100 ms to 150 ms, 100 ms to 140 ms, 100 ms to 130 ms, 100 ms to 120 ms, 100 ms to 110 ms, or approximately 100 ms. In some embodiments, the duration is preferably short so that the EP is tolerably or nearly painless as measured by a visual analog scale, yet sufficiently long so as to effect transfection of the cells in the epidermal tissues.

In some embodiments, the microcontroller 120 is configured to adjust a respective quantity of electroporating pulses for each electrode array 106, 108 independently, and the number of electrical pulses can be 1 or more, 2 or more, 3 or more, 4 or more, 5 or more, 6 or more, 7 or more, 8 or more, 9 or more, 10 or more, 20 or more, 30 or more, 40 or more, 50 or more, 60 or more, 70 or more, 80 or more, 90 or more, or 100 or more. By increasing the quantity of electroporating pulses and reducing the energy per pulse, the amount of pain perceived or experienced by a subject can also be reduced as compared with fewer pulses at higher energy. Preferably, a lower number of pulses, which does not reduce immune response that is generate, is used as it results in less pain experienced by the subject. Furthermore, less pain and better tolerability results by using lower energy per pulse. In some embodiments, the quantity of electroporating pulses is about 1 to about 10, preferably about 1 to about 10, and more preferably about 1 to about 3. In some embodiments 3 pulses are used.

In some embodiments, the electrode arrays 106, 108 are spaced apart from one another at least by a distance so as to substantially prevent interference of the two antigens delivered by the two arrays 106, 108 when the electroporating pulses are delivered. Plasmid interference has been observed for a number of antigens when they are delivered sequentially at the same site in the skin. Though not wishing to be bound by a particular theory, this could be due to interference at either the transcriptional level (possible competition at the promoter, etc.) or the translational level (mis-folding or dimerization at the protein level). The MID 100 having a plurality of spaced electrode arrays 106, 108 could eliminate this interference effect, which can negatively affect the resulting immune response. Moreover, the MID 100 having a plurality of electrode arrays 106, 108 could negate the need for two separate treatments, allowing a treated subject to experience one incident of treatment, thus reducing the pain that is experienced.

In some embodiments, the MID 100 includes switches (not shown) electrically coupled to each electrode array 106, 108 for selectively activating each electrode array 106, 108. For example, the MID 100 can be triggered by a foot pedal or a trigger button, or any other trigger connected to an electrical circuit.

Figure 3C:
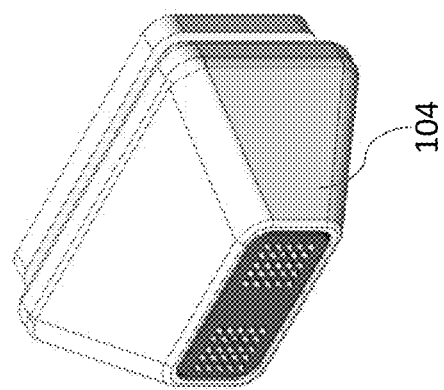
FIGS. 3A, 3B, and 3C are perspective views of a MID for EP according to another embodiment.
Figure 3B:
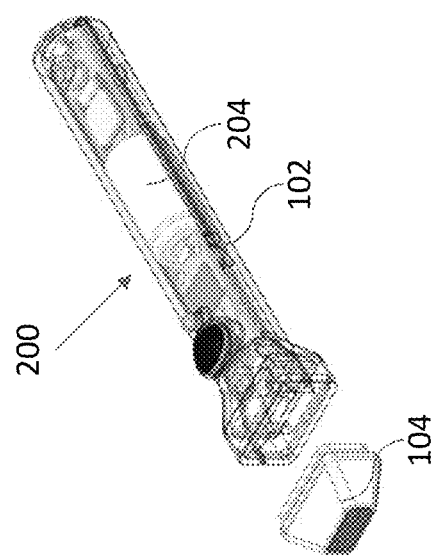
Figure 3A:
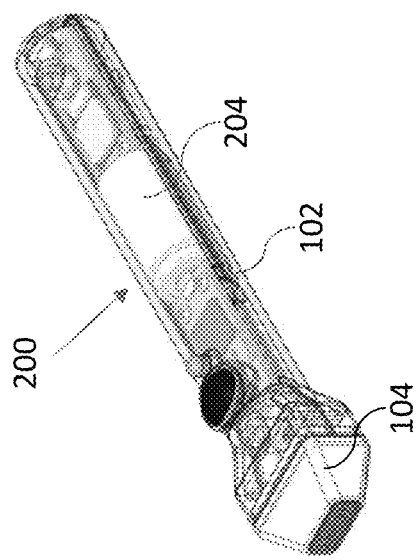
Figure 4:
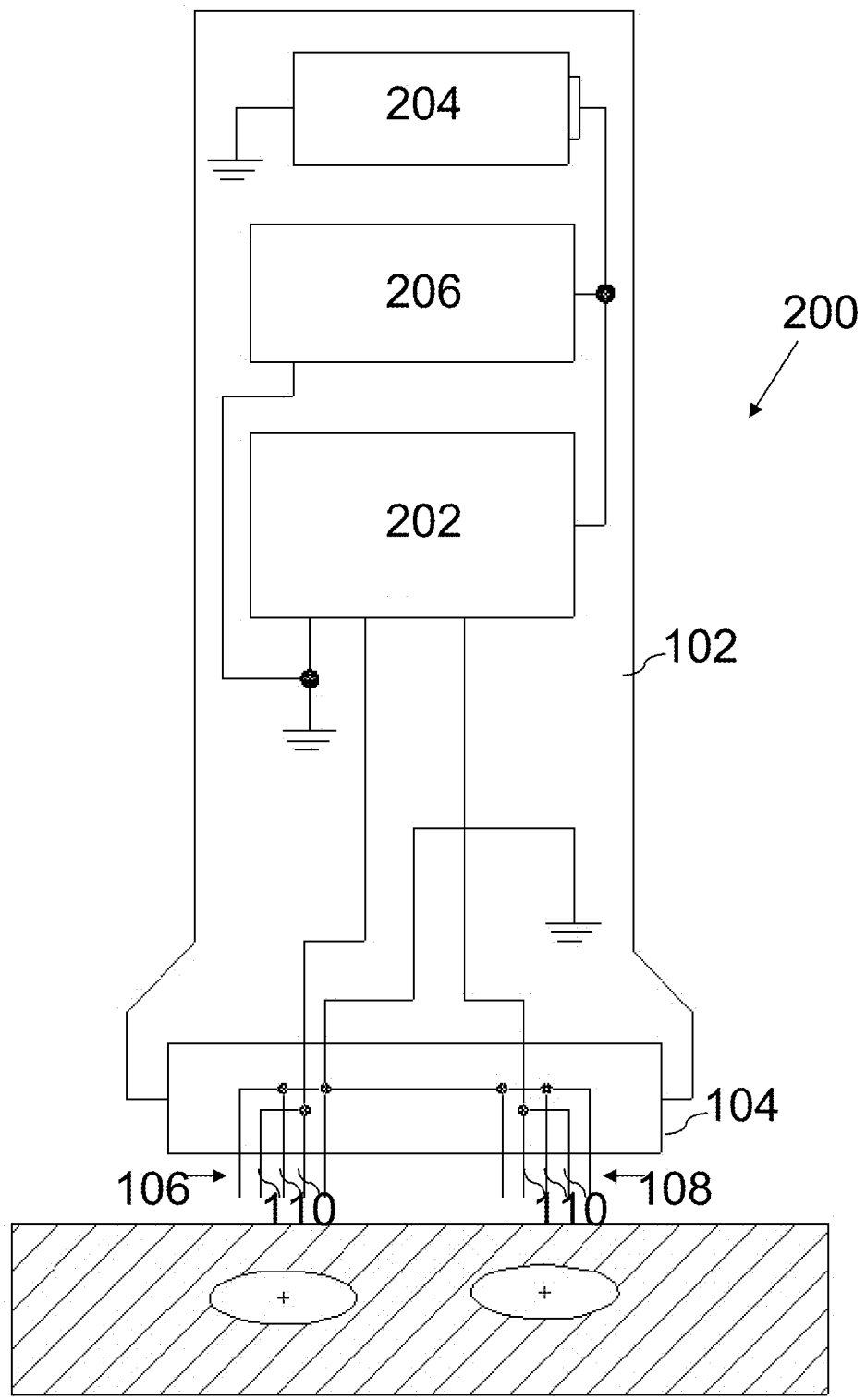
FIG. 4 is a schematic illustration of an electrical system of the embodiment of FIGS. 3A, 3B, and 3C.

FIGS. 3A, 3B and 4 illustrate an MID 200 including a pulse generator 202 according to another embodiment. This embodiment employs much of the same structure and has many of the same properties as the embodiment of the MID 100 described above in connection with FIGS. 1A-1C. Accordingly, the following description focuses primarily upon the structure and features that are different than the embodiment described above in connection with FIGS. 1A-1C. Structure and features of the embodiment shown in FIGS. 3 and 4 that correspond to structure and features of the embodiment of FIGS. 1A-1C are designated hereinafter with like reference numbers.

In this embodiment, the pulse generator 202 is powered by a battery 204. In the illustrated embodiment, the battery 204 is within the housing 102. As such, the MID 200 can be portable. The battery 204 can be a lithium ion, nickel metal hydride, lead acid, or nickel cadmium battery.

Referring to FIG. 4, the pulse generator 202 is a high and low voltage driver. The pulse generator 202 in this embodiment drives both electrode arrays 106, 108. A microcontroller 206 is electrically coupled to the pulse generator 202. The microcontroller 206 is capable of adjusting the electroporation parameters of each electrode array 106, 108 independently for example in response to an input condition/signal. The pulse generator 202 can generate pulses with EP parameters as adjusted by the microcontroller 206, and, in cooperation with the battery 204, amplify the generated pulses as needed.

3. Method of Electroporating and Delivering One or More Antigens

In an aspect, the MID 100, 200 having a plurality of electrode arrays 106, 108 described herein can be used in a method of electroporating and delivering one or more antigens, as discussed below, through the skin, organs, or other body parts of a subject. That is, the MID 100, 200 can be used to apply a transmembrane electric field pulse that induces microscopic pathways (pores) in a bio-membrane, allowing the delivery of one or more antigens from one side of the cellular membrane to the other. The method can comprise the steps of administering the antigen to the cells of the epidermal tissues, contacting the epidermal tissues with the electrodes, and delivering an electroporating pulse to generate an immune response. The method can further comprise simultaneously delivering antigen to the cells and delivering an electroporating pulse to generate an immune response.

Administering the Antigen to the Cells of the Epidermal Tissues

A plurality of antigens is first injected intradermally at spatially separated sites. In some embodiments, the antigen is intradermally delivered to the target tissue using the Mantoux technique, e.g., using a 29 gauge injection needle.

Contacting the Epidermal Tissues with the Electrodes

Next, the epidermal tissues are penetrated with at least one electrode 110 at a depth of about 0.1 mm or less, or about 0.01 mm to about 0.04 mm. The injection sites and the tissue-penetration sites are preferably co-localized. In some examples, to facilitate co-localizing or centering the injection sites and the tissue-penetration sites, the epidermal tissues can be marked or indented before the intradermal injection.

Delivering an Electroporating Pulse

Once the epidermal tissues are penetrated, the epidermal tissues are contacted with the electrodes 110 and an electroporating pulse is delivered. In some embodiments, the electroporating pulses are associated with an electrical field that substantially prevents damage to the cells of the epidermal tissues. In further embodiments, the electroporating pulses are associated with an electrical potential that is nearly painless as measured by a visual analog scale. For example, the electroporating pulses are associated with an electrical potential of about 1 volts to about 30 volts, or preferably about 15 volts to about 20 volts, an electrical current of about 1 mA to about 50 mA, or preferably about 10 mA to about 15 mA, and a duration ranging from about 80 ms to about 150 ms, or preferably 100 ms, or a combination thereof. These pulses can be delivered in a series, preferably 1-10 pulses, and more preferably 1-3 pulses.

A drawback to conventional intradermal delivery is a limitation to the volume that can be delivered to the skin. For a single needle injection, generally volumes no larger than 100-150 µl can be delivered directly to the skin due to issues with dermal delamination. Because the antigen can only be produced at concentrations not in excess of 10 mg/mL, the volume limitation can constrain the resulting dose.

In some embodiments, the MID 100, 200 can preferably deliver higher doses of a single vaccine. The use of the MID 100, 200 avoids the single injection volume limitation of 100-150 µL. In some embodiments, significantly higher doses can be delivered simultaneously with a single treatment without any added discomfort to the patient. The ability to deliver higher doses could have significant positive effects on the resulting immune responses for specific vaccines. The use of a multi-head device also has the added benefit of directly targeting more cells than a single array device. Increased numbers of cells transfected with an antigen could result in improved immune responses through increased presentation to antigen presenting cells.

In some embodiments, the disclosed method can be administered to a subject such as a mammal. The mammal can be a human, monkey, dog, cat, livestock, guinea pig, mouse, or a rat. The livestock can be bovine, a pig, a sheep, or a cow, for example.

4. Antigen

The present invention is also directed to methods of delivering at least one antigen using the MID 100, 200 having a plurality of electrode arrays 106, 108, as discussed above. The method can be directed to delivery of two or more antigens or a combination thereof using heterogeneous delivery by the MID 100, 200. In certain embodiments, the MID 100, 200 described herein can be used to enhance delivery of an antigen. As used herein, "antigen" refers to any substance or organism that provokes an immune response (produces immunity) when introduced into the body.

In some embodiments, the antigen can be derived from an infectious agent or a self-antigen, e.g., a prostate cancer antigen such as prostate-specific antigen (PSA) or prostate-specific membrane antigen (PSMA). The particular antigen used is not critical. Antigens are known in the art and can be incorporated for use in the methods and compositions provided herein using any common method. Non-limiting lists of suitable antigens for use in the various aspects and embodiments described herein can be found in the literature, for example, BioCarb Chemicals Catalogue; and The Jordan Report: Accelerated Development of Vaccine 1995 NIH, Bethesda, Md., 1995, both of which are incorporated herein by reference. Antigens can include, but are not limited to, nucleic acids, peptides, small molecules, chemotherapeutics, immunotherapeutics, or combinations thereof. An antigen can include an immunogen.

In some embodiments, the antigen comprises a nucleic acid. Nucleic acid refers to a polynucleotide compound, which includes oligonucleotides, comprising nucleosides or nucleoside analogs that have nitrogenous heterocyclic bases or base analogs, covalently linked by standard phosphodiester bonds or other linkages. Nucleic acids can include RNA, DNA, chimeric DNA-RNA polymers, or analogs thereof. The DNA can be a plasmid expressing a particular antigen of interest. For example, the plasmid can be a SynCon influenza construct (Inovio Pharmaceuticals, Inc., Blue Bell Pa.).

In some embodiments, the antigen comprises a peptide. Peptides include any amino acid sequence. Peptides can be synthetic or isolated from a natural source. The peptide can be a protein. The peptide can be an antibody or antibody fragment.

In some embodiments, the antigen comprises a small molecule. Small molecules include organic and inorganic compounds.

In some embodiments the antigen comprises a chemotherapeutic. Chemotherapeutics can include cytotoxic or cytostatic drugs such as, for example, methotrexate (amethopterin), doxorubicin (adrimycin), daunorubicin, cytosinarabinoside, etoposide, 5-fluorouracil, melphalan, chlorambucil, and other nitrogen mustards (e.g. cyclophosphamide), cis-platinum, vindesine (and other vinca alkaloids), mitomycin, bleomycin, purothionin (barley flour oligopeptide), macromomycin. 1,4-benzoquinone derivatives, and trenimon.

In some embodiments, the antigen includes a cytokine. Cytokine refers to a substance secreted by cells of the immune system that carry signals locally between cells. Cytokines include proteins, peptides, and glycoproteins. Cytokines include, but are not limited to, interferons, chemokines, TGF-β, TNF-α, and interleukins. Interleukins include IL-1, IL-2, IL-3, IL-4, IL-5, IL-6, IL-7, IL-8, IL-9, IL-10, IL-11, IL-12, IL-13, IL-14, IL-15, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-35, and IL-36. Cytokines can be derived from a human source or a transgenic non-human source expressing a human gene.

Antigens can include, but are not limited to, microbial antigens such as parasitic antigens, viral antigens, bacterial antigens, fungal antigens, cancer antigens, vaccine antigen additive drugs such as cocaine and nicotine derivatives, attenuated or killed bacteria, attenuated or killed virus, autoimmune antigens, or nonstructural protein antigens, or any combination thereof. In some embodiments, the antigen comprises at least one flu, autoimmune, cocaine, or cancer antigen.

In some embodiments an antigen comprises any antigen derived from bacterial surface polysaccharides which can be used in carbohydrate-based vaccines. Bacteria typically express carbohydrates on the cell surface as part of glycoproteins, glycolipids, O-specific side chains of lipopolysaccharides, capsular polysaccharides and the like. Non-limiting examples of suitable bacterial strains include *Streptococcus pneumonia, Neisseria meningitidis, Haemophilus influenza, Klebsiella* spp., *Pseudomonas* spp., *Salmonella* spp., *Shigella* spp., and Group B streptococci. In some embodiments any known bacterial carbohydrate epitope (e.g., those described in Sanders, et al. *Pediatr. Res.* 1995, 37, 812-819; Bartoloni, et al. *Vaccine* 1995, 13, 463-470; Pirofski, et al., *Infect. Immun.* 1995, 63, 2906-2911; U.S. Pat. No. 6,413,935; and International Publication No. WO 93/21948) can be used as an antigen in the compositions and methods herein described.

Some embodiments provide for an antigen that comprises a viral antigen. Non-limiting examples of viral antigens include those derived from HIV (e.g., gp120, nef, tat, pol), influenza, and West Nile Virus (WNV). In some embodiments, the antigen can comprise whole killed virus or attenuated virus.

Some aspects provide for a fungal antigen. Non-limiting examples of fungal antigens include those derived from *Candida albicans, Cryptococcus neoformans, Coccidioides* spp., *Histoplasma* spp., and *Aspergillus* spp.

Some embodiments provide for an antigen derived from a parasite. Non-limiting examples of parasitic antigens include those derived from *Plasmodium* spp., *Trypanosoma* spp., *Schistosoma* spp., *Leishmania* spp. and the like.

In some embodiments the antigen comprises a carbohydrate epitope. Non-limiting examples of carbohydrate epitopes that can be used in the aspects and embodiments described herein include: Galα1,4Galβ (for bacterial vaccines); GalNAcα (for cancer vaccines); Manβ1,2 (Manβ)$_n$Manβ-(for fungal vaccines useful against, for example, *C. albicans*), wherein n is any integer, including zero; GalNAcβ1,4(NeuAcα2,3)Galβ1,4Glcβ-O-ceramide (for cancer vaccines); Galα1,2(Tyvα1,3)Manα1,4Rhaα1,3Galα1,2-(Tyα1,3)Manα4Rha- and Galα1,2(Abeα1,3)Manα1,4Rhaα1,3Galα1,2(Abeα1,3) Manα1,4Rhaα1,3Galα1,2(Abeα1,3)Manα1,4Rha (both of which are useful against, for example, *Salmonella* spp.). Description of other exemplary carbohydrate epitopes as antigens or immunogens and the synthesis thereof are described further in U.S. Pat. No. 6,413,935, incorporated herein by reference.

Other examples of antigens include, but are not limited to, those that produce an immune response or antigenic response to the following diseases and disease-causing agents: anthrax; adenoviruses; *Bordetella pertussus*; Botulism; bovine rhinotracheitis; *Branhamella catarrhalis*; canine hepatitis; canine distemper; Chlamydiae; Cholera; coccidiomycosis; cowpox; cytomegalovirus; cytomegalovirus; Dengue fever; dengue toxoplasmosis; Diphtheria; encephalitis; Enterotoxigenic *Escherichia coli*; Epstein Barr virus; equine encephalitis; equine infectious anemia; equine influenza; equine pneumonia; equine rhinovirus; feline leukemia; flavivirus; Globulin; *Haemophilus influenza* type b; *Haemophilus influenzae*; *Haemophilus pertussis*; *Helicobacter pylori*; *Hemophilus* spp.; hepatitis; hepatitis A; hepatitis B; hepatitis C; herpes viruses; HIV; HIV-1 viruses; HIV-2 viruses; HTLV; Influenza; Japanese encephalitis; *Klebsiellae* spp. *Legionella pneumophila*; *Leishmania*; leprosy; lyme disease; malaria immunogen; measles; meningitis; meningococcal; Meningococcal Polysaccharide Group A, Meningococcal Polysaccharide Group C; mumps; Mumps Virus; mycobacteria; *Mycobacterium tuberculosis*; *Neisseria* spp; *Neisseria gonorrhoeae*; *Neisseria meningitidis*; ovine blue tongue; ovine encephalitis; papilloma; parainfluenza; paramyxovirus; paramyxoviruses; Pertussis; Plague; *Pneumococcus* spp.; *Pneumocystis carinii*; Pneumonia; Poliovirus; Proteus species; *Pseudomonas aeruginosa*; rabies; respiratory syncytial virus; rotavirus; Rubella; Salmonellae; schistosomiasis; Shigellae; simian immunodeficiency virus; Smallpox; *Staphylococcus aureus; Staphylococcus* spp.; *Streptococcus pneumoniae; Streptococcus pyogenes; Streptococcus* spp.; swine influenza; tetanus; *Treponema pallidum*; Typhoid; Vaccinia; varicella-zoster virus; and *Vibrio cholerae*. The antigens or immunogens can include various toxoids, viral antigens and/or bacterial antigens such as antigens commonly employed in the following vaccines: chickenpox vaccine; diphtheria, tetanus, and pertussis vaccines; *Haemophilus influenzae* type b vaccine (Hib); hepatitis A vaccine; hepatitis B vaccine; influenza vaccine; measles, mumps, and rubella vaccines (MMR); pneumococcal vaccine; polio vaccines; rotavirus vaccine; anthrax vaccines; and tetanus and diphtheria vaccine (Td) (see, e.g., U.S. Pat. No. 6,309,633).

In some embodiments, antigens can include any type of antigen associated with cancer such as, for example, tumor associated antigens (TSAs) (including antigens associated with leukemias and lymphomas) such as carcinoembryonic antigen, prostatic acid phosphatase, PSA, PSMA, and the like, and antigens that are associated with agents that can cause cancer (e.g., tumorigenic viruses such as, for example, adenovirus, HBV, HCV, HTLV, Kaposi's sarcoma-associated herpes virus, HPV (Gardasil), and the like).

Antigens can include combinations of antigens such as combinations of peptides, polysaccharides, lipids, nucleic acids, and the like. Antigens can include glycoproteins, glycolipids, glycoproteins, lipoproteins, lipopolysaccharides, and the like.

Antigens that are used to carry out the disclosed EP methods include those that are derivatized or modified in some way, such as by conjugating or coupling one or more additional groups thereto to enhance function or achieve additional functions such as targeting or enhanced delivery thereof, including techniques known in the art such as, for example, those described in U.S. Pat. No. 6,493,402 to Pizzo et al. (α-2 macroglobulin complexes); U.S. Pat. Nos. 6,309, 633; 6,207,157; and 5,908,629.

Illustrative examples of the MID 100, 200 and the method of using the MID 100, 200 are described in greater detail below.

EXAMPLES

Example 1

Effect of Electrode Composition on Transfection Efficiency

To address the effect of electrode material on reporter gene localization, transfection efficiency was compared for two minimally invasive devices (MID) with different electrode compositions (gold and stainless steel). This comparison was to assess whether a cheaper alternative (stainless steel) to gold electrodes could be used while still maintaining transfection efficacy. The electrode composition was easily tested, because the gold-plated electrodes were easily removed from their sockets and replaced with stainless steel electrodes of the same gauge and length. This produced an identical electrode head differing only in the electrode composition.

The experimental outline is detailed in Table 1.

TABLE 1

| Electrode Composition | DNA Delivered | DNA Concentration (mg/ml) | Number of Treatment Sites | Biopsy Removal Time (hours) | Number of Animals Required | Final Analysis |
|---|---|---|---|---|---|---|
| Gold-plated | pgWIZ-GFP | 0.5 | 10 | 12, 24, 48 | 4 | Gross Visualization/ Histology |
| | | 1 | 10 | 12, 24, 48 | | |
| | | 2 | 10 | 12, 24, 48 | | |
| Stainless steel | pgWIZ-GFP | 0.5 | 10 | 12, 24, 48 | 4 | Gross Visualization/ Histology |
| | | 1 | 10 | 12, 24, 48 | | |
| | | 2 | 10 | 12, 24, 48 | | |

A series of in vivo expression localization studies were completed. All in vivo experiments were conducted in Hartley guinea pigs (Charles River Laboratories, Wilmington, Mass.), which are considered an excellent model for dermatologic applications. All experiments were conducted under institutional IACUC protocols. All animal experiments were conducted in accordance with U.S. Department of Defense (DoD) 3216.1 "Use of Laboratory Animals in DoD Programs," 9 CFR parts 1-4 "Animal Welfare Regulations," National Academy of Sciences Publication "Guide for the Care & Use of Laboratory Animals," as amended, and the Department of Agriculture rules implementing the Animal Welfare Act (7 U.S.C. 2131-2159), as well as other applicable federal and state laws and regulations and DoD instructions. All animal treatments were carried out under anesthesia.

A plasmid expressing the reporter gene GFP was injected intradermally (0.5, 1, and 2 mg/mL) to guinea pig skin. Immediately following injection, the skin was electroporated at the injection site using a MID device with either gold or stainless steel electrodes. Animals were sacrificed three days post treatment. Skin was excised and visualized under a fluorescent microscope. High resolution photographs were taken and subsequently analyzed for pixel intensity using standard software (Adobe Photoshop CS5). The level of expression was calculated through pixel counts of pre-defined treatment areas. A "gated region" of electrode contact for pixel analysis was established on the presumption that transfection occurs only where the electric field is applied and that the electric field is formed only where the electrodes are in direct contact with the skin. The distance between the first and fourth electrode in the MID device was 4.5 mm. As such, the 'ruler tool' in Adobe Photoshop CS5 was used to isolate a 4.5 mm$^2$ region, which was defined as approximately 95 pixels in length. Adobe Photoshop CS5 recognized pixel intensities ranging from 0-255 (darkest-brightest) in three different channels (Red, Green, Blue). Since positive GFP signal would predominate in the green channel, pixel analysis was restricted to this channel. The CS5 version of Adobe Photoshop was able to automatically calculate mean and median pixel intensity of the selected region. Since the distribution of pixel intensity was not symmetrical in most cases, the median was deemed to give a better representation of central tendency for the histogram. To ensure accurate results, pooled data from multiple treatment sites on multiple animals was analyzed.

Results are shown in FIGS. 5A-5D. Results were also compared to GFP expression following intradermal injection without subsequent electroporation. There was no statistically significant difference between the gold and stainless steel groups (P value<0.05 between both treatment groups and the ID injection-only control). The results suggested that the cheaper stainless steel electrode was as effective as the gold electrode at eliciting reporter gene expression.

Example 2

Effect of Electrode Spacing on Transfection Efficiency

Figure 6A:
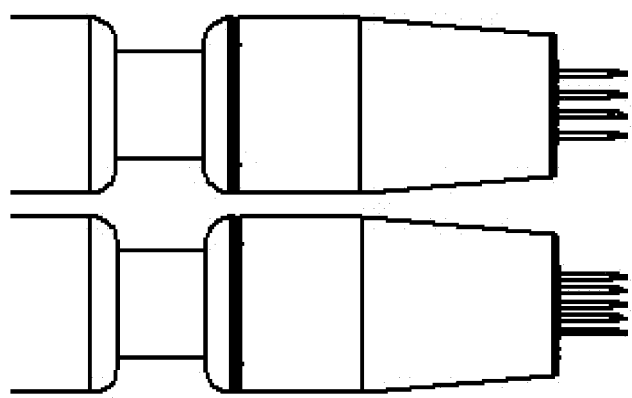
FIGS. 6A and 6B are views of a MID for EP as (FIG. 6A) a side view of a 1 mm-spaced array (top) and 1.5 mm-spaced array (bottom) electrode hand piece, and as (FIG. 6B) a close up of the face of a 1 mm-spaced array showing all 25 needle electrodes.
Figure 6B:
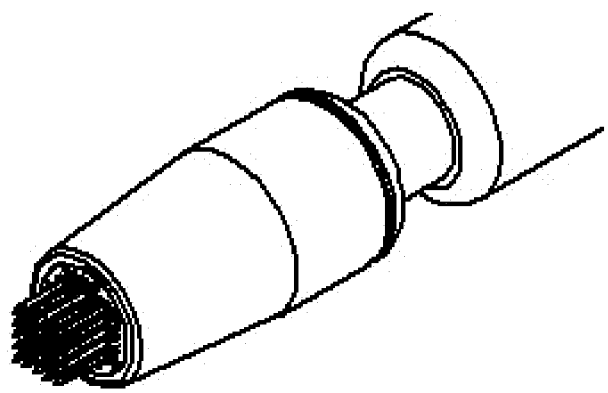

To assess the effect of electrode spacing on transfection efficiency and reporter gene localization, a 1 mm spaced circuit board was created and fitted in a head-piece housing and compared with a similar MID with a 1.5 mm spaced circuit board. To ensure that the surface treatment area remained the same between the two hand pieces at the different spacings, an additional row of electrodes was added to the 1 mm spaced circuit board. Therefore, a 1.5 mm spacing hand piece with 4×4 rows of electrodes (16 electrodes) was compared to a 1 mm spacing hand piece with 5×5 rows of electrodes (25 electrodes). As such, each hand piece had an approximate treatment surface area of approximately 4-4.5 mm$^2$. FIG. 6A shows a photograph of both hand pieces from a side perspective. The top hand piece is the 1 mm spacing, and the bottom hand piece is the 1.5 mm spacing. FIG. 6B shows a close-up view of the face of the 1 mm hand piece.

A series of in vivo expression localization studies were completed, as described in Example 1. Specifically, following an intradermal injection of a known dose (0.5, 1, and 2 mg/mL) of plasmid DNA expressing the reporter gene GFP into guinea pig skin, the 1 mm or 1.5 mm prototype device was used to almost immediately, within 10 seconds after injection, electroporate the resulting injection bubble. Electrodes were either gold or stainless steel in composition. Animals were sacrificed three days post treatment. Skin was excised and visualized under a fluorescent microscope. High resolution photographs were taken and subsequently analyzed for pixel intensity using standard software (Adobe Photoshop CS5). The level of expression was calculated through pixel counts of pre-defined treatment areas. To ensure accurate results, pooled data from multiple treatment sites on multiple animals was analyzed. Expression of the GFP was monitored over different time periods (12, 24, and 48 hours) to allow assessment of expression kinetics.

The experimental outline is detailed in Table 2.

TABLE 2

| Electrode Spacing | DNA Delivered | DNA Concentration (mg/ml) | Number of Treatment Sites | Biopsy Removal Time (hours) | Number of Animals Required | Final Analysis |
|---|---|---|---|---|---|---|
| 1 mm | pgWIZ-GFP | 0.5 | 10 | 12, 24, 48 | 4 | Gross Visualization/ Histology |
|  |  | 1 | 10 | 12, 24, 48 |  |  |
|  |  | 2 | 10 | 12, 24, 48 |  |  |
| 1.5 mm | pgWIZ-GFP | 0.5 | 10 | 12, 24, 48 | 4 | Gross Visualization/ Histology |
|  |  | 1 | 10 | 12, 24, 48 |  |  |
|  |  | 2 | 10 | 12, 24, 48 |  |  |

Results are shown in FIGS. 7A-7C. Results are shown for 6 treatments for each condition. Results were also compared to GFP expression following intradermal injection without subsequent electroporation. There was no statistically significant difference between results for the device with the 1.5 mm spaced circuit board and the 1 mm spaced circuit board (P value<0.05 between the treatment groups and the ID injection-only control). The results are representative of multiple experiments and demonstrated that successful, robust transfection was achieved with a minimally invasive device electroporation (MID EP) using either 1.5 mm or 1 mm electrode spacing.

These results suggested that electrode spacing does not impact GFP expression in skin because no visible difference (as determined by eye and quantifiably through pixel counting) was observed between the two electrode spacings. Thus, electroporation with MID EP using either 1.5 mm or 1 mm electrode spacing resulted in robust reporter gene expression.

Example 3

Effect of Electrode Spacing on Current

A device as described herein can have the capacity to capture and store all electrical parameters real time as they occur during each electroporation pulse. A series of in vivo expression localization studies were completed, as described in Example 1, to examine current and voltage for electroporation with devices of different electrode spacing and composition. While the applied voltage remained constant (15 volts), the impedance (resistance) and current delivered for each treatment was examined for each electrode spacing and each electrode composition.

FIG. 8 shows both the resulting impedance (resistance in Ohms) and Current (in milli Amps).

The current was approximately three times greater in the 1 mm hand piece (average 85 mA) compared to the 1.5 mm hand piece (average 23 mA), yet the applied voltage was the same across all conditions. The increased current in the 1.5 mm hand piece resulted in a large reduction (approximately 75%) in the impedance of the tissue. From the perspective of producing a tolerable dermal device, increased current can be problematic by causing more pain or sensation to the patient. Increased current can cause more pain or sensation in a patient, and thus, increased current can be problematic in producing a tolerable dermal device. These results suggested that while the electrode spacing did not appear to impact the resulting GFP expression, either the spacing or the presence of the additional electrodes can impact the current flow and, as such, impact the impedance of the tissue.

To further address the issue of increased current, it was investigated whether the applied voltage could be reduced by a third (to 5 volts) and still result in 10-20 mA current.

Electrodes were stainless steel. Results are shown in FIG. 9. The results suggested that additional electrodes, and not the actual electrode spacing, affected the resulting current.

To assess whether a reduced voltage affected the transfection efficacy, a DNA plasmid expressing the reporter gene GFP was delivered intradermally to guinea pig skin and immediately followed with electroporation using a MID device with either 1.5 mm (4×4) electrode spacing or 1 mm (4×4 or 5×5) electrode spacing at 15 or 5 volts. The animals were sacrificed three days post treatment. The skin was excised and visualized under a fluorescence microscope. High resolution photographs were taken and subsequently analyzed for pixel intensity using standard software (Adobe Photoshop CS5).

Results are shown in FIGS. 10A and 10B. These results suggested that the input voltage can be reduced on larger electrode hand pieces while still maintaining transfection efficacy. As such, the results suggested that robust transfection can be achieved with a larger array while maintaining pain-free and low voltage parameters. It is likely that in a human clinical device, at least 25 electrodes would be required to maintain optimal coverage depending on the usage requirements or preferences, e.g., the injection volume.

Example 4

Effect of Plasmid Concentration on Transfection Efficiency

The effect of lower concentrations of plasmid expressing the reporter gene GFP on transfection efficiency was examined with devices of different composition and electrode spacing.

A series of in vivo expression localization studies were completed, as described in Example 1. A plasmid expressing the reporter gene GFP was injected intradermally (0.5, 0.25, and 0.1 mg/mL) to guinea pig skin and immediately followed with electroporation using a MID device with either gold or stainless steel electrodes and either 1 mm—(5×5) or 1.5 mm—(4×4) spaced electrodes at 15 volts. The animals were sacrificed three days post treatment. The skin was excised and visualized under a fluorescence microscope. High resolution photographs were taken and subsequently analyzed for pixel intensity using standard software (Adobe Photoshop CS5). The level of expression was calculated through pixel counts of pre-defined treatment areas. To ensure accurate results, pooled data from multiple treatment sites on multiple animals was analyzed.

Results are shown in FIGS. 11A and 11B. The GFP expression following ID injection alone (no EP) was also observed but minimal expression was detected (data not shown). No statistically significant differences between either spacing or electrode composition was observed at any of the concentrations of the plasmid expressing the reporter gene GFP.

Example 5

Electroporation Efficiency Analyzed at the Cellular Level

Skin samples removed from treated animals from experiments detailed in the above Examples were analyzed immunohistochemically. Skin post-treatment was excised postmortem, sectioned, and paraffin mounted. GFP-expressing cells were observed and counted using a high powered fluorescent microscope (Olympus-BX51 TF). The number and region (i.e., layer of strata in epidermis) of GFP-expressing cells were noted. Histological sections were also counter-stained with a collection of commercially available antibodies prior to mounting to allow the direct identification of transfected cell types, such as lymphocyte IHC, keratinocytes (the majority of cells in the epidermis), and Langerhans cells (most common APC's in the epidermis). The antibodies were also used to observe the effect of electroporation on lymphocyte infiltration.

Robust keratinocyte staining was achieved in the epidermis. The epidermal region in the skin sections was clearly defined. Overall, the results suggested that the additional electrodes massively impacted the current flow and, as such, impacted the impedance of the tissue. This increased current flow did not appear to affect the resulting expression of the reporter gene. However, it was apparent that the voltage could be reduced on the 5×5 1 mm hand piece while still achieving strong currents and robust transfection.

To see positive staining for the Langerhans specific antibody in the skin, spleen and lymph nodes were removed from a sacrificed animal to use as positive controls for the antibody. Strong antibody staining was detected in both the spleen and the lymph nodes but not in the skin. Although not wishing to be bound by a particular theory, this suggested that the antibody was working but that either the signal in the skin was too weak to detect, or there were no Langerhans cells present in the tissue tested.

Figure 12A:
FIGS. 12A, 12B, and 12C are fluorescent micrographs of lymphocyte staining following injection and electroporation of plasmids using an MID.
Figure 12B:
Figure 12C:
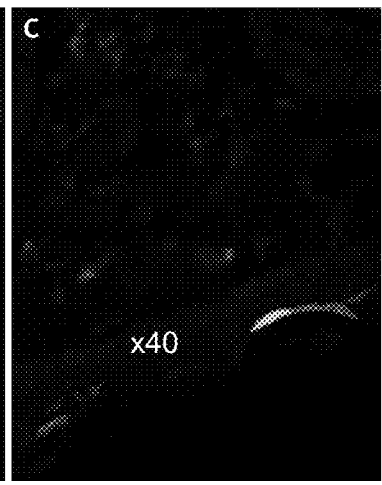
Figure 13A:
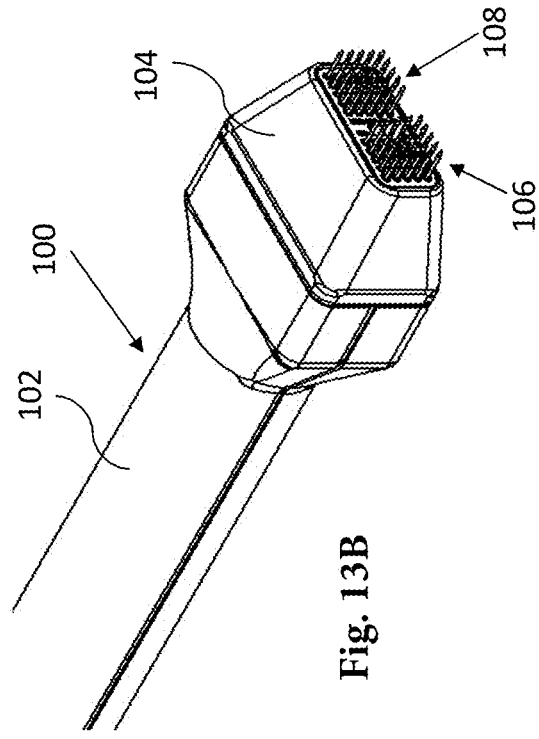
FIG. 13A is a perspective view of a MID for EP according to an embodiment.
Figure 13B:
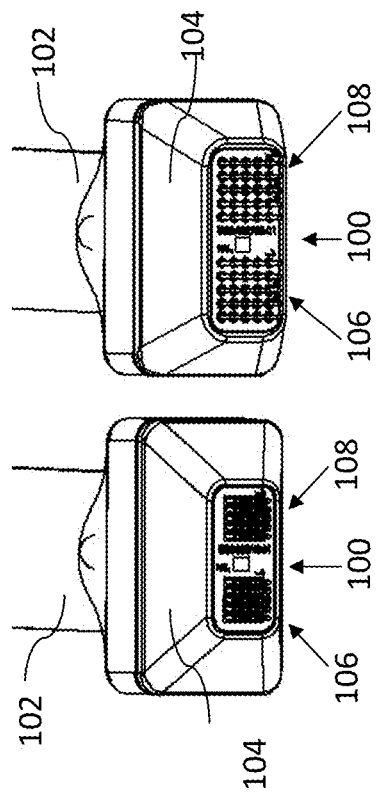
FIG. 13B is a photograph of an MID with a 4×4 array and 1.5 mm spacing.
Figure 13C:
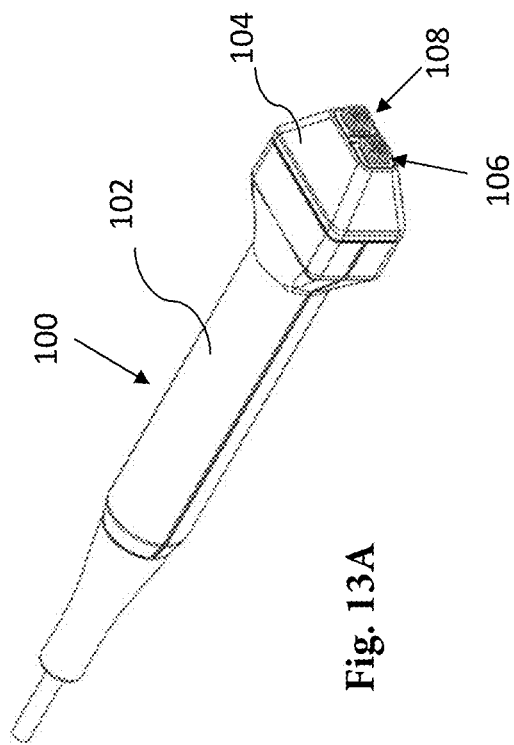
FIG. 13C is a photograph of an MID with a 5×5 array and 1.0 mm spacing.
Figure 13D:
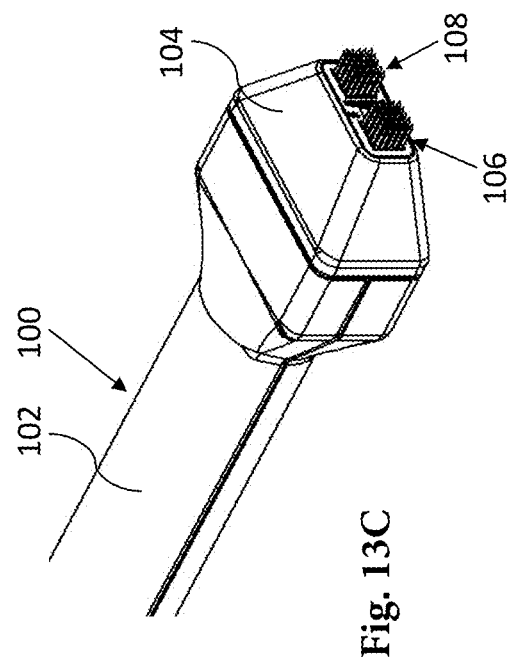
FIG. 13D is a photograph showing a side by side comparison of the MIDs in FIGS. 13B and 13C.

Additional results are shown in FIGS. 12A-12C. It was observed that both electroporation and expression of reporter genes resulted in infiltration of lymphocytes to the treatment area. The combination of EP and reporter gene expression resulted in the largest infiltration. While co-localization of kerotinocyte staining and reporter gene expression was observed, the staining was not consistent. However, co-localization of lymphocyte IHC and reporter gene expression was consistently confirmed.

Example 6

Dual-Head Device

A dual-head device having two arrays side by side with a small buffer zone was manufactured. The arrays were designed to deliver pulses simultaneously. Alternatively, each head can be pulsed independently with additional equipment modifications. Plastic housings and custom electrical components were prototyped. The devices are shown in FIGS. 13A-13D.

Figure 14:
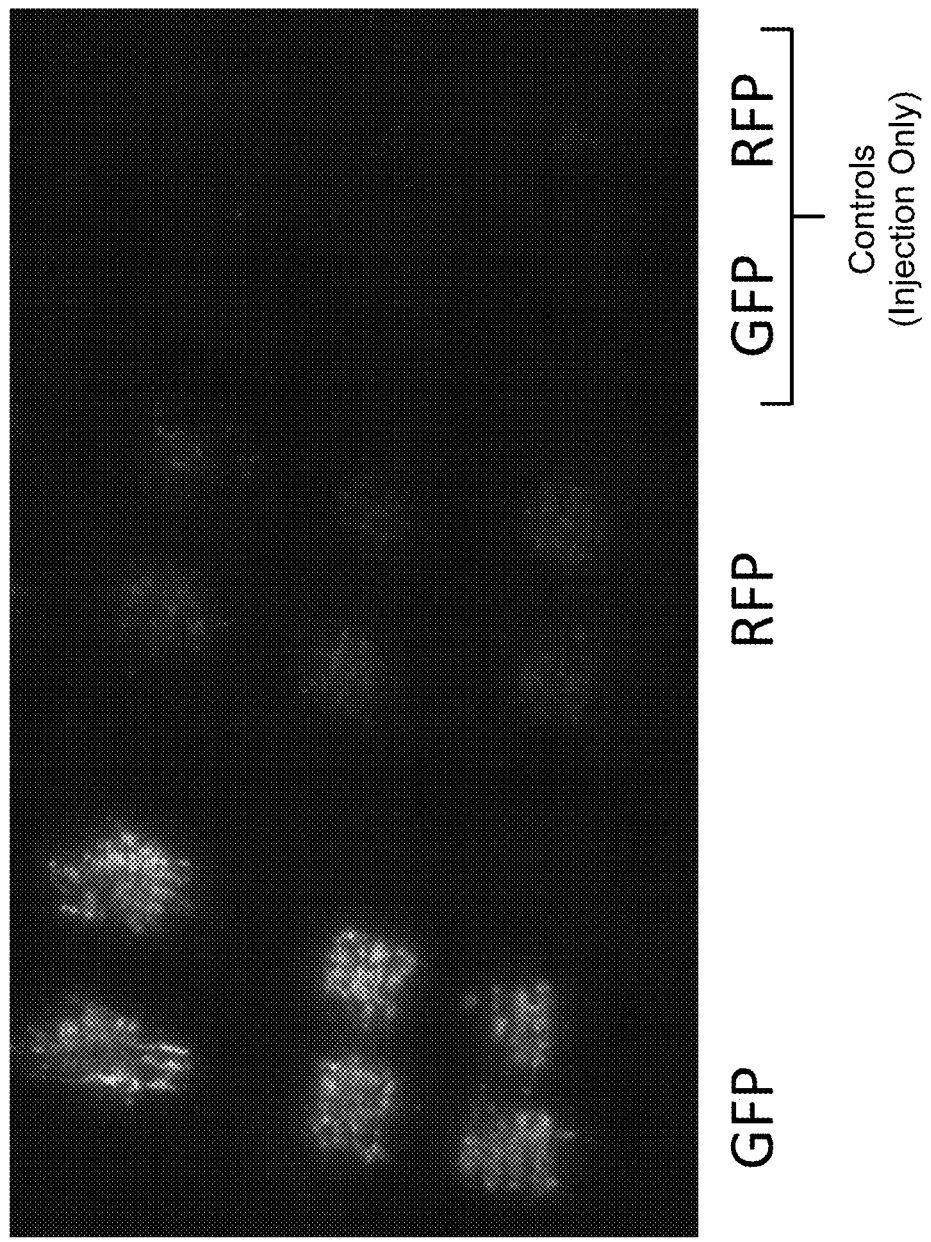
FIG. 14 is a fluorescent micrograph showing the GFP expression following an intradermal administration of a reporter gene plasmid and EP with the dual-head MIDs of FIG. 13B, compared to the GFP expression following the intradermal injection alone (no EP).

A series of in vivo expression localization studies were completed, as described in Example 1. A plasmid expressing the reporter gene GFP or RFP was injected intradermally at a concentration of 1 mg/mL to guinea pig skin. Injection was immediately followed with electroporation using the dual head device (with 16 stainless steel electrodes in a 4×4 array and a spacing of 1.5 mm, at 25 V). The results are shown in FIG. 14, which is a fluorescent micrograph showing the GFP expression following an intradermal administration of a reporter gene plasmid and EP with the MID 100, 200, compared to the GFP expression following the intradermal injection alone (no EP). The electrodes 110 of the MID 100, 200 were spaced from one another by a spacing of 1.5 mm. The animal was sacrificed post treatment and the skin excised and visualized under a fluorescence microscope. The fluorescent micrograph confirms that multiple plasmids were delivered simultaneously at spatially separated sites.

Example 7

Kinetics of Transfection

A series of in vivo expression localization studies will be completed, using the methods as described in Example 1. Specifically, following an intradermal injection of a known dose (0.5, 1, and 2 mg/mL) of plasmid DNA expressing the reporter gene GFP into guinea pig skin, a 1 mm or 1.5 mm prototype device will be used to immediately electroporate the resulting injection bubble. Electrodes of the MID will be either gold or stainless steel in composition. Animals will be sacrificed at different time points (12 hours, 24 hours, and 48 hours, 3 days) post treatment. Skin will be excised and visualized under a fluorescent microscope for each time point. High resolution photographs will be taken and subsequently analyzed for pixel intensity using standard software (Adobe Photoshop CS5). The level of expression will be calculated through pixel counts of pre-defined treatment areas. To ensure accurate results, pooled data from multiple treatment sites on multiple animals will be analyzed. Expression of the GFP will be compared over the different time periods to facilitate assessment of expression kinetics.

It should be understood from the foregoing that, while particular embodiments have been illustrated and described, various modifications can be made without departing from the spirit and scope of the disclosure as will be apparent to those skilled in the art. Such changes and modifications are within the scope and teachings of this disclosure as defined in the claims appended hereto.

What is claimed is:

1. A method for delivering one or more antigens to epidermal tissue, the method comprising:
   administering a first antigen to a first region of the epidermal tissue;
   administering a second antigen to a second region of the epidermal tissue adjacent the first region;
   contacting the first and second regions with first and second arrays of electrodes, respectively, wherein the first and second arrays extend from a single housing;
   delivering first electroporating pulses to cells of the first region via the first array of electrodes;
   delivering second electroporating pulses to cells of the second region via the second array of electrodes; and
   adjusting parameters of at least one of the first and second electroporating pulses with respect to the other of the first and second electroporating pulses during the first and second delivering steps.

2. The method of claim 1, wherein the adjusting step comprises varying an electrical potential of at least one of the first and second arrays with respect to an electrical potential of the other of the first and second arrays.

3. The method of claim 2, wherein the electrical potential is a range of about 1 volts to about 30 volts.

4. The method of claim 1, wherein the adjusting step comprises varying an electrical current through at least one of the first and second arrays with respect to an electrical current through the other of the first and second arrays.

5. The method of claim 4, wherein the electrical current is in a range of about 1 mA to about 50 mA.

6. The method of claim 1, wherein the adjusting step comprises varying durations of at least one of the first and second electroporating pulses with respect to durations of the other of the first and second electroporating pulses.

7. The method of claim 6, wherein each of the durations is in a range of about 4 ms to about 250 ms.

8. The method of claim 1, wherein the adjusting step comprises varying a quantity of at least one of the first and second electroporating pulses with respect to a quantity of the other of the first and second electroporating pulses.

9. The method of claim 8, wherein each quantity is in a range of about 1 pulse to about 10 pulses.

10. The method of claim 1, wherein the first and second regions are spaced apart from one another at least by a distance so as to substantially prevent interference of the antigens during the delivering steps.

11. The method of claim 1, wherein each delivering step comprises delivering the respective electroporating pulses in a geometric pattern to the cells of the respective region via the respective array.

12. The method of claim 11, wherein the delivering steps comprise delivering the electroporating pulses to the first and second regions substantially simultaneously via the first and second arrays.

13. The method of claim 1, wherein the contacting step comprises penetrating epidermal tissue within each of the first and second regions to a depth between about 0.01 mm to about 0.1 mm with at least one electrode of each of the first and second arrays.

14. The method of claim 1, wherein the first delivering step comprises generating a first electrical field within the first region via the first array, the second delivering step comprises generating a second electrical field within the second region via the second array, and the first and second electrical fields collectively prevent damage to the cells of the first and second regions during the delivering steps.

15. The method of claim 1, wherein each of the first and second antigens is a nucleic acid, a peptide, or a small molecule.

16. The method of claim 1, wherein the adjusting step is performed by a microcontroller electrically coupled to a first pulse generator and a second pulse generator, the first pulse generator is electrically coupled to the first array so as to generate the first electroporating pulses, and the second pulse generator is electrically coupled to the second array so as to generate the second electroporating pulses.

17. The method of claim 16, wherein the contacting step comprises manipulating a housing that houses both of the first and second arrays so as to place the first and second arrays into engagement with the first and second regions, respectively.

18. The method of claim 17, wherein in each of the first and second arrays, adjoining electrodes are spaced apart from one another at a distance not greater than 1.5 mm.

19. The method of claim 1, wherein the parameters of each of the first and second electroporating pulses include:

an electrical potential in a range of about 1 volt to about 30 volts;

an electrical current in a range of about 1 mA to about 50 mA;

a duration in a range of about 4 ms to about 250 ms; and a quantity in a range of about 2 pulses to about 10 pulses.

20. The method of claim 19, wherein the adjusting step comprises adjusting two or more of the parameters of the first and second electroporating pulses with respect to each other.

* * * * *